US012599402B2

(12) United States Patent
Gustafson et al.

(10) Patent No.: US 12,599,402 B2
(45) Date of Patent: Apr. 14, 2026

(54) DEFLECTABLE PULMONARY ACCESS TOOL

(71) Applicant: Covidien LP, Mansfield, MA (US)

(72) Inventors: Evan M. Gustafson, Sioux Falls, SD (US); Nathan J. Knutson, Long Lake, MN (US); Franklin J. Burquest, Crystal, MN (US); Bethany A. Palmer, Coon Rapids, MN (US); Tina M. Berthiaume, Champlin, MN (US); Hannah M. Capek, Minneapolis, MN (US); Matthew A. Rootes, Crystal, MN (US)

(73) Assignee: Covidien LP, Mansfield, MA (US)

( * ) Notice: Subject to any disclaimer, the term of this patent is extended or adjusted under 35 U.S.C. 154(b) by 126 days.

(21) Appl. No.: 18/288,951

(22) PCT Filed: May 23, 2022

(86) PCT No.: PCT/IB2022/054811
§ 371 (c)(1),
(2) Date: Oct. 30, 2023

(87) PCT Pub. No.: WO2022/249036
PCT Pub. Date: Dec. 1, 2022

(65) Prior Publication Data
US 2024/0216013 A1      Jul. 4, 2024

Related U.S. Application Data

(60) Provisional application No. 63/194,699, filed on May 28, 2021.

(51) Int. Cl.
*A61B 17/34* (2006.01)
*A61B 17/00* (2006.01)
(Continued)

(52) U.S. Cl.
CPC .... *A61B 17/3417* (2013.01); *A61B 17/00234* (2013.01); *A61B 34/20* (2016.02);
(Continued)

(58) Field of Classification Search
CPC .......... A61B 17/3417; A61B 17/00234; A61B 34/20; A61B 50/26; A61B 2017/00039;
(Continued)

(56) References Cited

U.S. PATENT DOCUMENTS

| | | |
|---|---|---|
| 6,254,573 B1 | 7/2001 | Haim et al. |
| 10,034,999 B2 | 7/2018 | Mathis et al. |

(Continued)

FOREIGN PATENT DOCUMENTS

| | | | |
|---|---|---|---|
| DE | 3108766 A1 | 9/1982 | |
| WO | 2019051251 | 3/2019 | |
| WO | WO-2020215007 A1 * | 10/2020 | ............. A61B 18/00 |

OTHER PUBLICATIONS

PCT Search Report and Written Opinion issued in PCT Application No. PCT/IB2022/054811 dated Aug. 5, 2022.

*Primary Examiner* — Katherine M Shi
(74) *Attorney, Agent, or Firm* — Weber Rosselli & Cannon LLP

(57) ABSTRACT

An access tool for piercing an airway wall including a dilating member (308) having a minimally traumatic tip formed on a distal end, a piercing member (302) having a piercing tip on a distal and a handle (304) formed on a proximal end, and a spring-loaded actuator (406) connecting the piercing member and the dilating member such that upon actuation the piercing member is urged in the direction of the dilating member.

20 Claims, 5 Drawing Sheets

(51) Int. Cl.
  *A61B 34/20*      (2016.01)
  *A61B 50/26*      (2016.01)
(52) U.S. Cl.
  CPC .... *A61B 50/26* (2016.02); *A61B 2017/00039*
    (2013.01); *A61B 2017/00296* (2013.01); *A61B*
    *2017/00367* (2013.01); *A61B 2034/2051*
    (2016.02); *A61B 2034/2061* (2016.02)
(58) Field of Classification Search
  CPC .......... A61B 2017/00296; A61B 2017/00367;
    A61B 2034/2051; A61B 2034/2061;
    A61B 1/0005; A61B 1/2676; A61B
    2017/00323; A61B 2017/3409; A61B
    1/00133; A61B 2017/00809; A61B
    2090/034; A61B 2090/571; A61B
    17/3478; A61B 2018/00577; A61B 1/018;
    A61B 10/0233; A61B 18/1492; A61B 2018/00541; A61B 2018/1861; A61B
90/50; A61M 25/0082; A61M 25/0147
See application file for complete search history.

(56)                References Cited

U.S. PATENT DOCUMENTS

| 10,561,463 | B2 | 2/2020 | Dickhans et al. | |
| 2003/0109809 | A1 | 6/2003 | Jen et al. | |
| 2015/0073211 | A1 | 3/2015 | Dickhans et al. | |
| 2018/0028225 | A1 | 2/2018 | Whayne et al. | |
| 2018/0132935 | A1* | 5/2018 | Dickhans ........... | A61B 1/00133 |
| 2018/0256263 | A1* | 9/2018 | Krimsky ............ | A61B 1/00009 |
| 2019/0046013 | A1 | 2/2019 | Saadat et al. | |
| 2020/0170628 | A1 | 6/2020 | Herdina et al. | |
| 2020/0229875 | A1 | 7/2020 | Keast et al. | |
| 2022/0000462 | A1* | 1/2022 | Berliner ............. | A61B 10/0233 |

* cited by examiner

DEFLECTABLE PULMONARY ACCESS TOOL

BACKGROUND

Technical Field

This disclosure relates to an endobronchial tool, and more particularly, to devices, systems, and methods for navigating an endobronchial tool to access tissue located outside a bronchus.

Description of Related Art

A common interventional procedure in the field of pulmonary medicine is bronchoscopy, in which a bronchoscope is inserted into the airways through the patient's nose or mouth. In some instances, a catheter system is inserted into a working channel of the bronchoscope so that airways smaller than those which the bronchoscope is capable of traversing can be navigated through. Diagnostic and therapy tools may be inserted through the catheter to capture specimen or treat a previously diagnosed lesion.

However, in some cases, the target tissue may be located outside the airway walls. In this situation, it is necessary to insert a tool capable of piercing the bronchial walls through the catheter. The piercing tool may include a dilating catheter which slides over a piercing element and using its bullet-shaped end dilates the opening in the airway wall formed by a piercing element. The piercing element and the dilating catheter may be walked one after the other until the piercing member is inserted into a lesion (e.g., following the Seldinger technique). The dilating catheter is advanced over the piercing member and inserted into the lesion. The catheter, sometimes called an extended working channel, is advanced over the dilating catheter and piercing element. Once the catheter is in or proximate the target tissue, the piercing tool is removed and a diagnostic or therapy tool may be inserted through the catheter in order to act on the targeted tissue (e.g., perform a biopsy or ablation of the targeted tissue).

As will be appreciated, between the bronchoscope, the catheter, the piercing element, and the dilating catheter there are far too many devices to be comfortably handled by a single person. Often a third or fourth hand is necessary to utilize all the above features. The challenges in handling the many devices are exacerbated by the tissues involved. For example, the airways can be rather tough and require substantial force to pierce, however, tissue beyond the airway wall the parenchyma is considerably less tough. The result is that by applying sufficient force to pierce the airway wall, upon piercing, the piercing element is somewhat uncontrolled and can damage additional tissues beyond the airway wall including blood vessels and other airways.

Accordingly, improvements are needed to allow for more controlled access beyond the airway walls and to simplify the practice of reaching such locations as well as enabling the insertion of diagnostic and therapy tools.

SUMMARY

One aspect of the disclosure is directed to a catheter navigation system including: a catheter guide assembly configured to be received within a working channel of bronchoscope and including a catheter; an access tool configured to be received within a catheter of the catheter guide assembly, the access tool including a dilating member having a minimally traumatic tip formed on a distal end, a lumen extending therethrough, and a handle formed on a proximal end and a piercing member sized for reception and translation within the lumen of the dilating member, the piercing member having a piercing tip on a distal and a handle formed on a proximal end; a rail including a plurality of slidable and lockable anchors, a first slidable and lockable anchor configured to connect to the catheter guide assembly, a second slidable and lockable anchor configured to connect to the handle of the dilating member and a third slidable and lockable anchor configured to connect to the handle of the piercing member; a spring-loaded actuator, the spring-loaded actuator operably connecting the piercing member and the dilating member such that upon unlocking of the slidable and lockable anchor connected to the piercing member, the handle of the piercing member is urged in the direction of the handle of the dilating member, and the piercing tip extends beyond the minimally traumatic tip of the dilating member; and a stop configured for engagement with the rail and the piercing member to limit a distance the spring-loaded actuator drives the piercing member through the dilating member and a distance the piercing tip extends beyond the minimally traumatic tip of the dilating member Implementations of this aspect of the disclosure may include one or more of the following features. The catheter navigation system further including a sensor secured in the minimally traumatic tip of the dilating member. The catheter navigation system where the sensor is an electromagnetic sensor. The catheter navigation system where the sensor is a shape sensor. The catheter navigation system further including a pull-wire operably connected to the minimally traumatic tip of the dilating member. The catheter navigation system further including a lumen formed in the dilating member for receiving the pull-wire. The catheter navigation system further including an open groove formed on an exterior surface of the dilating member for receiving and retaining the pull-wire.

Another aspect of the disclosure is directed to an access tool including: a dilating member having a minimally traumatic tip formed on a distal end, a lumen extending therethrough, and a handle formed on a proximal end and a piercing member sized for reception and translation within the lumen of the dilating member, the piercing member having a piercing tip on a distal and a handle formed on a proximal end; a rail including a plurality of slidable and lockable anchors, a first slidable and lockable anchor configured to connect to connect to the handle of the dilating member and a second slidable and lockable anchor configured to connect to the handle of the piercing member; and a spring-loaded actuator, the spring-loaded actuator operably connecting the piercing member and the dilating member such that upon unlocking of the slidable and lockable anchor connected to the piercing member, the handle of the piercing member is urged in the direction of the handle of the dilating member, and the piercing tip extends beyond the minimally traumatic tip of the dilating member.

Implementations of this aspect of the disclosure may include one or more of the following features. The access tool further including a stop configured for engagement with the rail and the piercing member to limit a distance the spring-loaded actuator drives the piercing member through the dilating member and a distance the piercing tip extends beyond the minimally traumatic tip of the dilating member. The access tool further including a sensor secured in the minimally traumatic tip of the dilating member. The access tool where the sensor is an electromagnetic sensor. The access tool where the sensor is a shape sensor. The access tool further including a pull-wire operably connected to the minimally traumatic tip of the dilating member. The access tool further including a lumen formed in the dilating member for receiving the pull-wire. The access tool further including an open groove formed on an exterior surface of the dilating member for receiving and retaining the pull-wire.

A further aspect of the disclosure is directed to an access tool including: a dilating member having a minimally traumatic tip formed on a distal end, a lumen extending therethrough, and a handle formed on a proximal end and a piercing member sized for reception and translation within the lumen of the dilating member, the piercing member having a piercing tip on a distal and a handle formed on a proximal end; and a spring-loaded actuator, the spring-loaded actuator operably connecting the piercing member and the dilating member such that upon actuation the piercing member is urged in a direction of the dilating member, and the piercing tip extends beyond the minimally traumatic tip of the dilating member.

Implementations of this aspect of the disclosure may include one or more of the following features. The access tool further including a stop configured for engagement with the piercing member to limit a distance the spring-loaded actuator drives the piercing member through the dilating member and a distance the piercing tip extends beyond the minimally traumatic tip of the dilating member. The access tool further including a sensor secured in the minimally traumatic tip of the dilating member. The access tool where the sensor is an electromagnetic sensor. The access tool further including a pull-wire operably connected to the minimally traumatic tip of the dilating member.

BRIEF DESCRIPTION OF THE DRAWINGS

Various aspects and embodiments of the disclosure are described hereinbelow with references to the drawings, wherein.

DETAILED DESCRIPTION

This disclosure is directed to improvements to an access tool and systems for deploying the access tool to enable bronchial piercing and dilating for biopsy and therapeutic tool placement that improve the accuracy of the piercing as well as the safety of the advancement of the access tool in comparison to prior devices. In addition, the systems of the disclosure reduce the physical burdens of the manipulations of the access tool. Still further, the systems and devices of the disclosure improve the maneuverability and manipulability of the access tool and enable tracking of the position of the access tool during manipulation.

Figure 1:
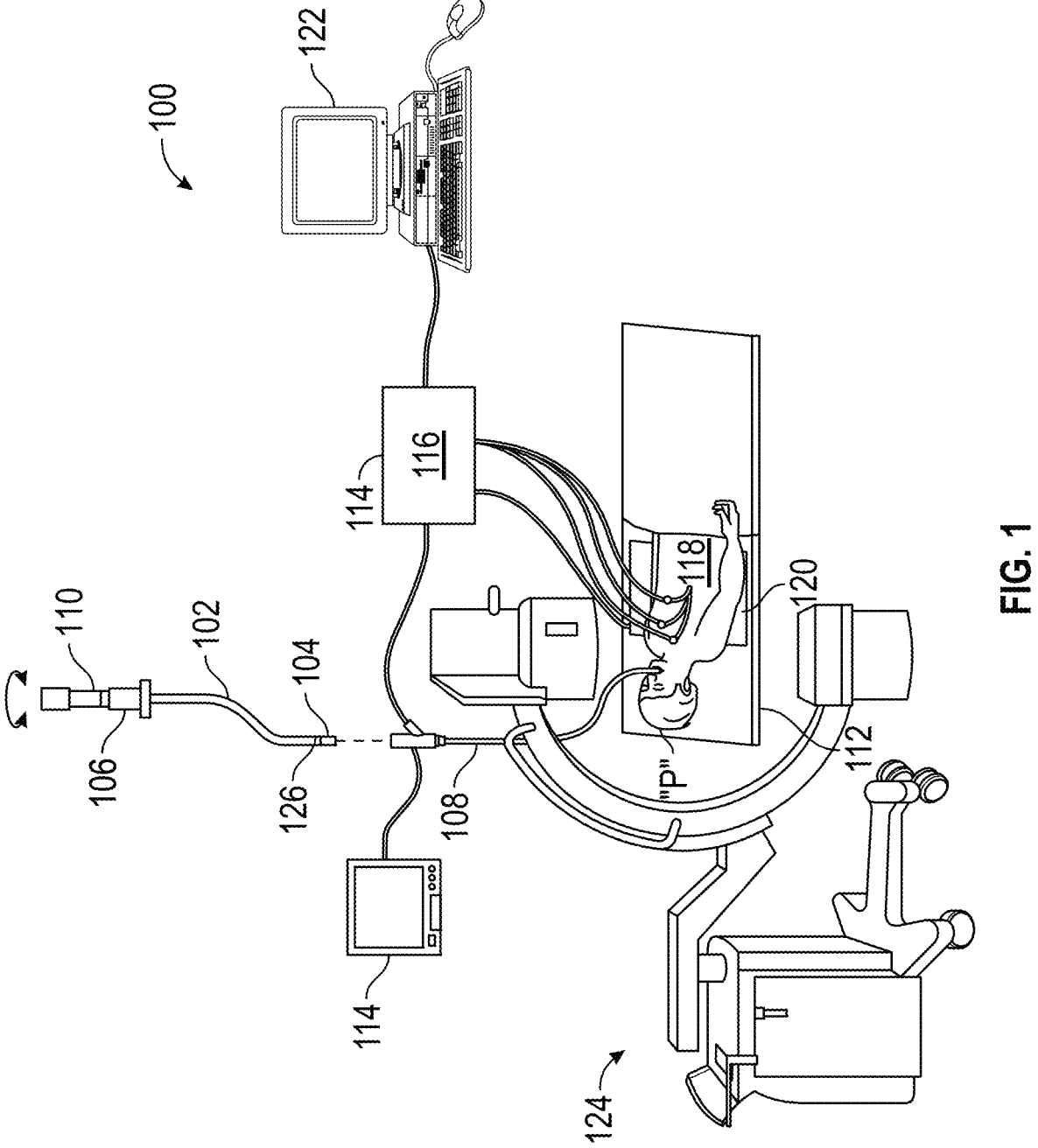
FIG. 1 is a depiction of a lung navigation system in accordance with the disclosure.

FIG. 1 depicts a system for navigation of a catheter within the airways of a patient. As shown in FIG. 1, catheter 102 is part of a catheter guide assembly 106. In practice, catheter

102 is inserted into a bronchoscope 108 for access to a luminal network of the patient P. Specifically, catheter 102 of catheter guide assembly 106 may be inserted into a working channel of bronchoscope 108 for navigation through a patient's luminal network. A locatable guide (LG) 110 (a second catheter), including a sensor 104 is inserted into catheter 102 and locked into position such that sensor 104 extends a desired distance beyond the distal tip of catheter 102. The position and orientation of sensor 104 relative to a reference coordinate system, and thus the distal portion of catheter 102, within an electromagnetic field can be derived. Catheter guide assemblies 106 are currently marketed and sold by Medtronic PLC under the brand names SUPERDIMENSION® Procedure Kits, or EDGE™ Procedure Kits, and are contemplated as useable with the disclosure.

System 100 generally includes an operating table 112 configured to support a patient P, a bronchoscope 108 configured for insertion through patient P's mouth into patient P's airways; monitoring equipment 114 coupled to bronchoscope 108 (e.g., a video display, for displaying the video images received from the video imaging system of bronchoscope 108); a locating or tracking system 114 including a locating module 116, a plurality of reference sensors 118 and a transmitter mat 120 including a plurality of incorporated markers; and a computing device 122 including software and/or hardware used to facilitate identification of a target, pathway planning to the target, navigation of a medical device to the target, and/or confirmation and/or determination of placement of catheter 102, or a suitable device therethrough, relative to the target.

A fluoroscopic imaging device 124 capable of acquiring fluoroscopic or x-ray images or video of the patient P is also included in this particular aspect of system 100. The images, sequence of images, or video captured by fluoroscopic imaging device 124 may be stored within fluoroscopic imaging device 124 or transmitted to computing device 122 for storage, processing, and display. Additionally, fluoroscopic imaging device 124 may move relative to the patient P so that images may be acquired from different angles or perspectives relative to patient P to create a sequence of fluoroscopic images, such as a fluoroscopic video. The pose of fluoroscopic imaging device 124 relative to patient P and while capturing the images may be estimated via markers incorporated with the transmitter mat 120. The markers are positioned under patient P, between patient P and operating table 112 and between patient P and a radiation source or a sensing unit of fluoroscopic imaging device 124. The markers incorporated with the transmitter mat 120 may be two separate elements which may be coupled in a fixed manner or alternatively may be manufactured as a single unit. Fluoroscopic imaging device 124 may include a single imaging device or more than one imaging device.

Computing device 122 may be any suitable computing device including a processor and storage medium, wherein the processor is capable of executing instructions stored on the storage medium. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/video and other data described herein. Additionally, computing device 122 includes a display configured to display graphical user interfaces. Computing device 122 may be connected to one or more networks through which one or more databases may be accessed.

With respect to the planning phase, computing device 122 utilizes previously acquired CT image data for generating and viewing a three-dimensional model or rendering of patient P's airways, enables the identification of a target on the three-dimensional model (automatically, semi-automatically, or manually), and allows for determining a pathway through patient P's airways to tissue located at and around the target. More specifically, CT images acquired from previous CT scans are processed and assembled into a three-dimensional CT volume, which is then utilized to generate a three-dimensional model of patient P's airways. The three-dimensional model may be displayed on a display associated with computing device 122, or in any other suitable fashion. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through patient P's airways to access tissue located at the target can be made. Once selected, the pathway plan, three-dimensional model, and images derived therefrom, can be saved and exported to a navigation system for use during the navigation phase(s). The ILLUMISITE software suite currently sold by Medtronic PLC includes one such planning software.

With respect to the navigation phase, a six degrees-of-freedom electromagnetic locating or tracking system 114, or other suitable system for determining position and orientation of a distal portion of the catheter 102, is utilized for performing registration of the images and the pathway for navigation. Tracking system 114 includes the tracking module 116, a plurality of reference sensors 118, and the transmitter mat 120 (including the markers). Tracking system 114 is configured for use with a locatable guide 110 and particularly sensor 104. As described above, locatable guide 110 and sensor 104 are configured for insertion through catheter 102 into patient P's airways (either with or without bronchoscope 108) and are selectively lockable relative to one another via a locking mechanism.

Transmitter mat 120 is positioned beneath patient P. Transmitter mat 120 generates an electromagnetic field around at least a portion of the patient P within which the position of a plurality of reference sensors 118 and the sensor 104 can be determined with use of a tracking module 116. A second electromagnetic sensor 126 may also be incorporated into the end of the catheter 102. The second electromagnetic sensor 126 may be a five degree-of-freedom sensor or a six degree-of-freedom sensor. One or more of reference sensors 118 are attached to the chest of the patient P. Registration is generally performed to coordinate locations of the three-dimensional model and two-dimensional images from the planning phase, with the patient P's airways as observed through the bronchoscope 108 and allow for the navigation phase to be undertaken with knowledge of the location of the sensor 104.

Registration of the patient P's location on the transmitter mat 120 may be performed by moving sensor 104 through the airways of the patient P. More specifically, data pertaining to locations of sensor 104, while locatable guide 110 is moving through the airways, is recorded using transmitter mat 120, reference sensors 118, and tracking system 114. A shape resulting from this location data is compared to an interior geometry of passages of the three-dimensional model generated in the planning phase, and a location correlation between the shape and the three-dimensional model based on the comparison is determined, e.g., utilizing the software on computing device 122. In addition, the software identifies non-tissue space (e.g., air filled cavities) in the three-dimensional model. The software aligns, or registers, an image representing a location of sensor 104 with the three-dimensional model and/or two-dimensional images generated from the three-dimension model, which are based on the recorded location data and an assumption that locatable guide 110 remains located in non-tissue space in patient P's airways. Alternatively, a manual registration technique may be employed by navigating the bronchoscope 108 with the sensor 104 to pre-specified locations in the lungs of the patient P, and manually correlating the images from the bronchoscope to the model data of the three-dimensional model.

Though described herein with respect to electromagnetic navigation (EMN) systems using EM sensors, the instant disclosure is not so limited and may be used in conjunction with flexible sensor, ultrasonic sensors, or without sensors. Additionally, the methods described herein may be used in conjunction with robotic systems such that robotic actuators drive the catheter 102 or bronchoscope 108 proximate the target.

Figure 2:
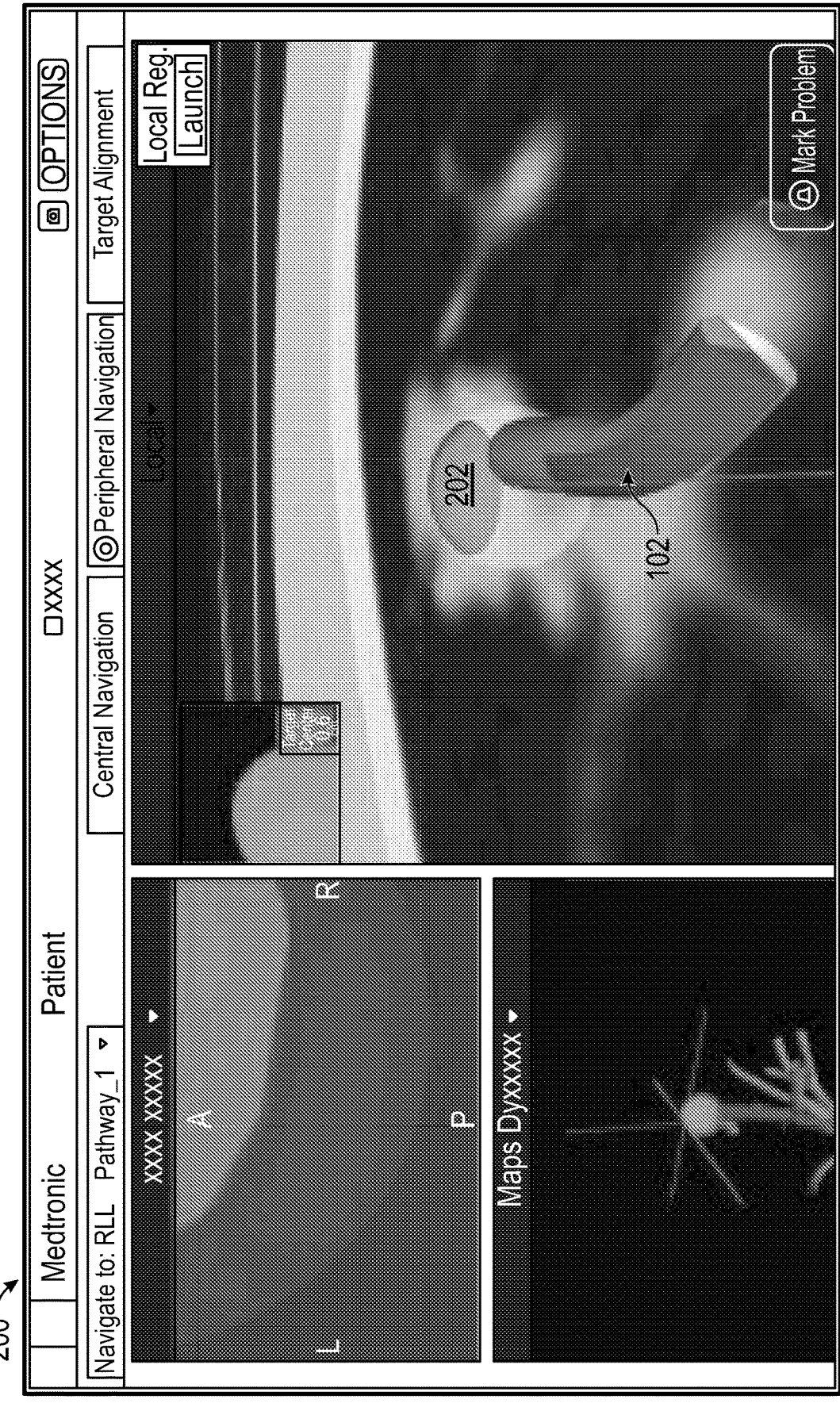
FIG. 2 is a depiction of a user-interface for navigation of a catheter with the airways of a patient.

Following registration of the patient P to the image data and pathway plan, a user interface 200 as shown in FIG. 2 is displayed on the computing device 122 using the navigation software which sets forth the pathway that the clinician is to follow to reach the target. Once catheter 102 has been successfully navigated proximate, as shown in FIG. 2, the target 202.

As noted above, in instances where the target 202 is located outside of the airways of the patient, an access tool is required. Once such access tool 300 can be seen in FIGS. 3A and 3B.

The access tool 300 is sized to be received in the catheter 102. The access tool 300 includes a piercing member 302 having a handle 304 at one end and a piercing tip 306 at the opposite end. In one embodiment the piercing member 302 and piercing tip 306 are formed of a wire (e.g., stainless or nitinol) having sufficient rigidity to pierce an airway wall.

Figures 3A, 3B:
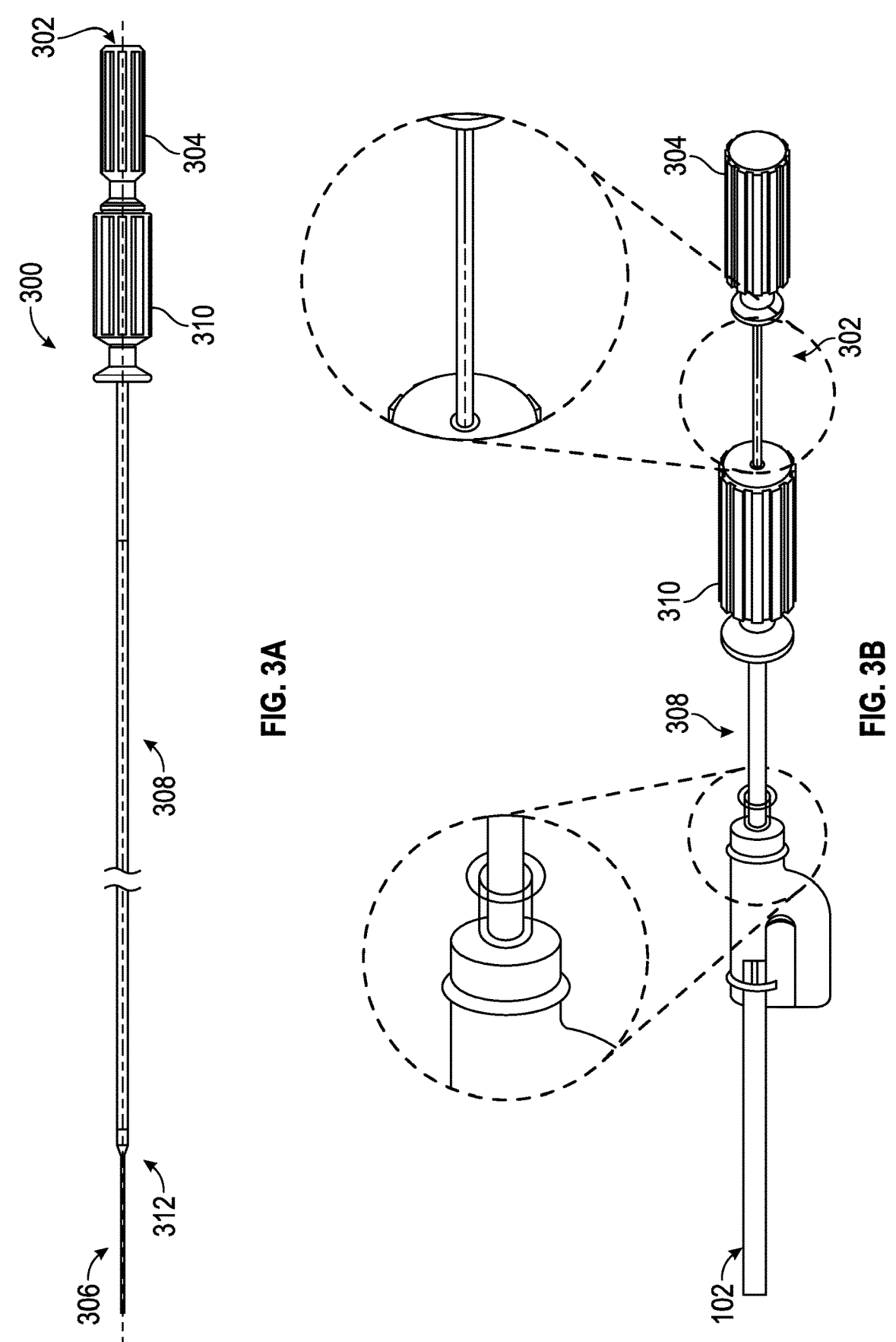
FIGS. 3A and 3B are side views of an access tool in accordance with the disclosure.

The piercing member 302 is received in a dilating member 308. The dilating member 308 has a handle 310 on one end and a minimally traumatic end 312. The minimally traumatic end 312 may bullet-shaped, tapered, or another blunt shape that is designed to expand openings in the airway wall formed by the piercing tip 306, but not itself pierce tissue. The minimally traumatic end 312 may be formed of a metal such as stainless steel. At maximum insertion the piercing tip 306 of the piercing member extends about 5 CM beyond the minimally traumatic end 312 of the dilating member 308. In FIG. 3B the piercing member 302 is shown fully advanced through the dilating member 308 such that the wire extends beyond the tapered metal distal tip of the catheter, and the proximal handle of the wire abuts the proximal handle of the catheter.

Both the piercing member 302 and the dilating member 308 are flexible and configured for insertion into a lumen of catheter 102 which acts as an extended working channel of the bronchoscope 108 in which it is inserted enabling placement proximate endobronchial lesions, peripheral lung nodules, or lung masses. The piercing member 302 extends through the inner lumen of the dilating member 308 and can be manipulated independently from the dilating member 308 using the handle 304 to puncture the tracheobronchial wall to create a passage from within the bronchial airway through the airway wall to a target location outside of the airway.

Once the opening is formed in the airway wall with the piercing member 302, the dilating member 308 is advanced over the piercing member 302 to expand the opening in the airway wall and to dissect tissue beyond the airway wall to create a pathway to the target tissue (e.g., 202 in FIG. 2). Upon arriving at the target tissue, the catheter 102 can be slid over the dilating member 308 such that the catheter 102 is immediately adjacent the target tissue 202, or even within the target tissue.

As noted above, because of the multiple handles 304, 310, as well as the handle for the catheter 102 and the broncho-scope 108, the use of the access tool 300 can be clumsy and cumbersome requiring the use of additional personnel. The use of multiple personnel also necessitates close coordina-tion between the people, all within a close environment and on a patient that is still breathing.

Figure 4:
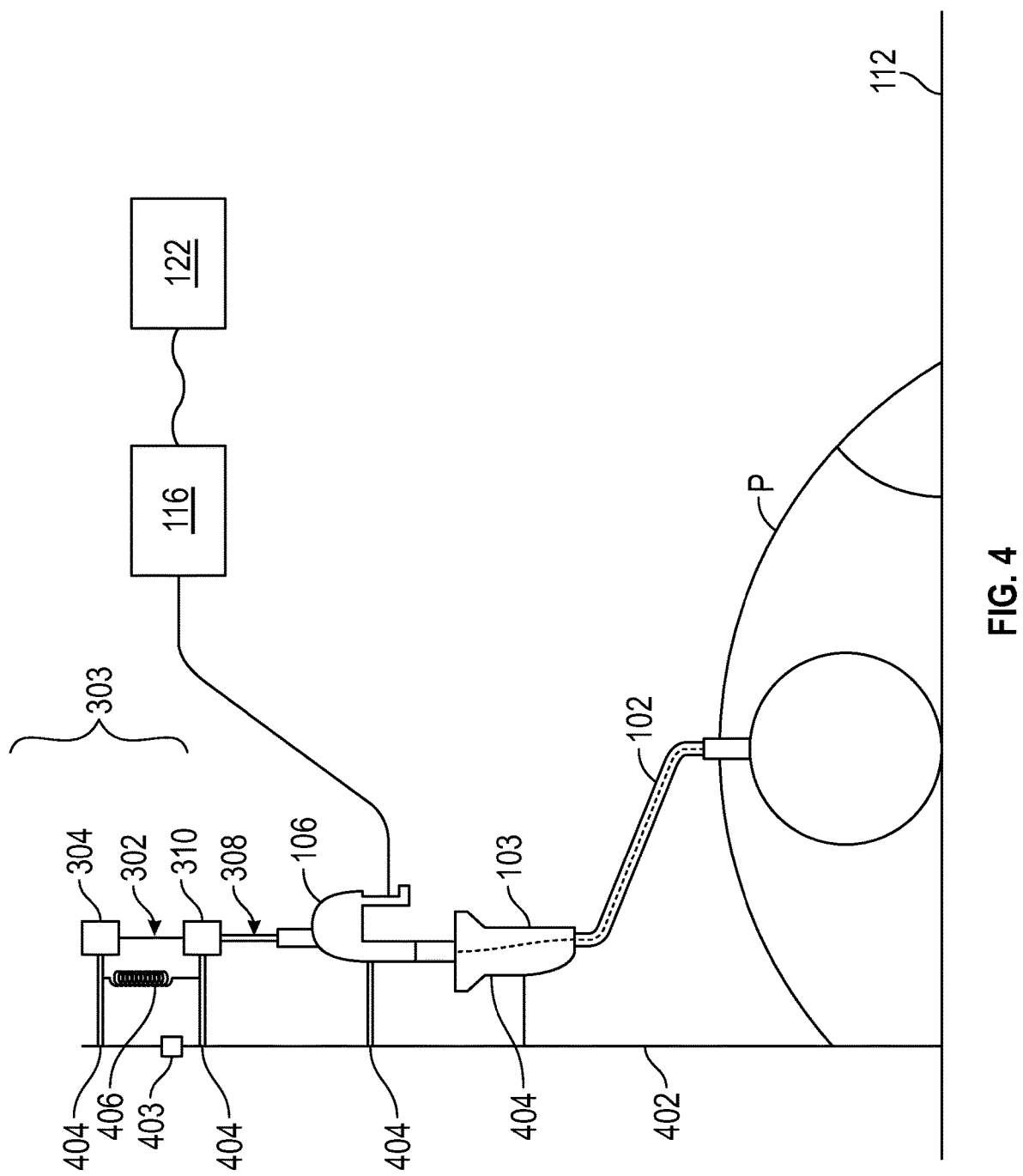
FIG. 4 is a view of an access tool systems in accordance with the disclosure.

One aspect of the disclosure is directed to rail system 400 as depicted in FIG. 4 and modifications to the access tool 300 to reduce the manipulation burdens and provide for greater accuracy and repeatability in use. As depicted in FIG. 4 the access tool 300 and catheter guide assembly 106 are slidingly mounted on a rail 402. Extending from the rail 402 are a number of slidable and lockable anchors 404. Each anchor 404 can be locked in a desired position on the rail 402, and the individually released to allow for movement of the component attached thereto in a vertical direction. Though depicted hereto that the endoscope 108 is attached to the rail 402, it may not necessarily be secured to the rail and may instead be held by the clinician. Further, the rail 402 is depicted as mounted to the table 112, the rail 402 may instead be mounted to the floor of the operating theater, mounted on a cart with lockable wheels, or other configu-rations without departing from the scope of the disclosure.

In practice, the bronchoscope 108 is navigated within the airways of the patient P until the bronchoscope 108 becomes wedged within the airways. Once so wedged, the catheter assembly 106 which may have been previously locked in relation to the bronchoscope 108, can be unlocked and navigation to a target tissue 202 can be achieved by advance-ment of the catheter 102 through the airways of the patient P, as described above. As described above, the catheter assembly 106 may include the LG 110 having therein a sensor 104 whose position can be detected and represented on computing device 122. The use of the LG 110 may not be necessary and reliance on the sensor 126 in the catheter 102.

In one embodiment, once proximate an airway wall prevents direct access to the target tissue 202, the LG 110 (if used) may be removed from the catheter 102 and an access tool 300 inserted therein. The handle 310 of the dilating member 308 may be inserted into one of the slidable locking anchors 404 and the handle 304 of the piercing member 302 may be placed in a second of the slidable locking anchors 404. Similarly, the catheter guide assembly 106 may also be attached to a slidable locking anchors 404. In this manner the relative positions of the piercing member 302, the dilating member 308, the catheter guide assembly 106 and the bronchoscope may be set and locked in place along the rail 402.

The access tool 300, prior to locking the handles 304 and 310 to the rail 402 may be advanced through the catheter 102 to be proximate the airway wall that prevents access to the target tissue 202. With the minimally traumatic tip 312 of the dilating member 308 proximate the airway wall movement of the dilating member stops. The piercing member 302 may then be advanced from the dilating member to pierce the airway wall. In one embodiment this is achieved by releas-ing the slidable locking anchor 404 attached to the handle 304 and the clinician advancing the piercing member 302 through the dilating member 308 to pierce the airway wall.

Alternatively, the slidable locking anchor 404 attached to the handle 304 may include a spring-loaded actuator 406. The spring-loaded actuator 406 in combination with the slidable locking anchor 404 allows the handle 304 a desired distance from the handle 310 of the dilating member 308. Upon unlocking of the slidable locking anchor 404 con-nected to the handle 304, the spring-loaded actuator 406 causes the piercing member 302 to be quickly, powerfully, and controllably advanced the desired distance. That desired distance may be the entire distance separating handle 304 and handle 310. Alternatively, one or more stops 408 may be placed on the rail 402 limiting how much the slidable locking anchor 404 attached to the handle 304 may be advanced towards the handle 310, and thus the extent to which the piercing tip 306 extends beyond the minimally traumatic tip 312 of the dilating member 308.

After release of the piercing member 302 a desired distance beyond the end 312 of the dilating member 308 the piercing member 302 may again be secured to the rail 402 by the slidable locking anchor 404. The slidable locking anchor 404 connected to the handle 310 of the dilating member 308 may then be released allowing the advance-ment of the dilating member 308 over the piercing member 302. The piercing member 302 may be again released as described above and the dilating member 308 advanced thereover until the access too 300 is proximate the target tissue 202. Alternatively, once beyond the airway wall where the tissues of the parenchyma are easier to dissect than the airway wall, the piercing member 302 may be locked relative to the dilating member 308 (e.g., using stops 408). The piercing member 302 may act as an obturator prevent-ing tissue from entering the lumen in the dilating member 308 through which the piercing member travels. When locked together the entirety of the access tool 300 may be advanced as a unit through and dissect the tissues of the parenchyma creating a tunnel to arrive at the target tissue 202.

At any point after piercing of the airway wall by the piercing member 302 and advancement of the dilating member 308 through the opening in the airway wall the slidable locking anchor 404 connected to the catheter guide assembly 106 may be released while the slidable locking anchors 404 connected to the dilating member 308 and piercing member 302 are secured to the rail 402. The catheter 102 of the catheter guide assembly 106 may then be advanced over the dilating member 308. All of the release and advancements of the piercing member 302, dilating member 308 and catheter guide assembly 106 may be performed in a step wise fashion until the catheter 102 is proximate the target tissue 202.

Through the use of slidable locking anchors 404 mounted on the rail 402 and the stops 408, the entire assembly of the access tool 300, catheter guide assembly 106 and the bron-choscope 108 may be securely held and their relative movement can be conveniently managed by a single user. Further, the extent that the piercing member 302 and par-ticularly the piercing tip 306 extends beyond the dilating member 308 and particularly the minimally traumatic tip 312 can be carefully controlled to prevent over extension and the inadvertent damaging of tissues beyond the dilating member 308.

Figure 5:
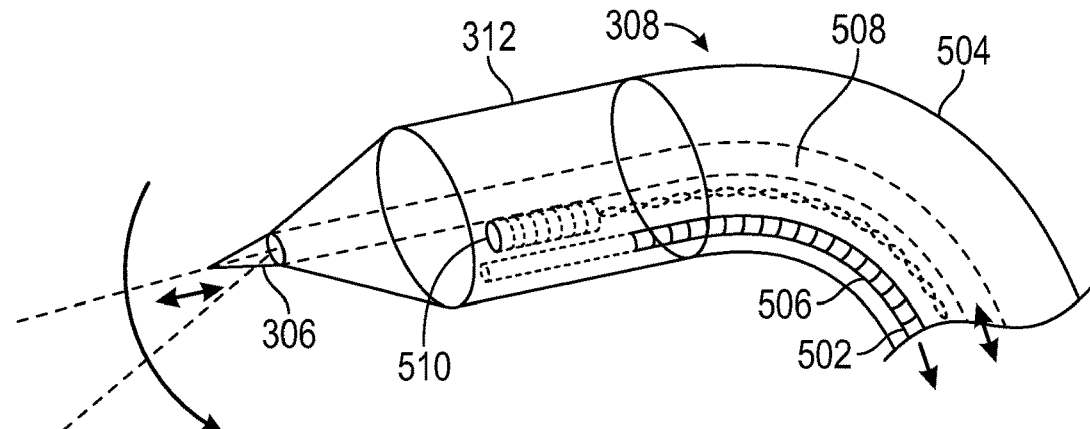
FIG. 5 is a perspective view of an end portion of an access tool in accordance with the disclosure.

A further aspect of the disclosure is directed to an articulated dilating member 308 as depicted in FIG. 5. As depicted in FIG. 5, a pull wire 502 is incorporated into the catheter body 504 of the dilating member 308. The pull wire 502 traverses a lumen 506 formed in the catheter body 504. The pull wire 502 may be welded, adhered, swaged or otherwise secured to the minimally traumatic tip 312 of the dilating member 308. An actuator (not shown) allows for the pull wire 502 to be retracted within the lumen 506. Because of the flexible nature of the catheter body 504 retraction of the pull wire 502 causes the minimally traumatic tip 312 to articulate in the direction of the pull wire 502. As can be seen in FIG. 5 the piercing member 302 extends through a lumen 508 in dilating member 308 and the piercing tip 306 extends out of minimally traumatic tip 312 to enable the piercing of an airway wall as described above.

A further aspect of the embodiment of FIG. 5 is a sensor 510 mounted within the minimally traumatic tip 312. The sensor 510 may be a five or a six degree of freedom electromagnetic sensor. Additionally or alternatively, the sensor 510 may be a shape sensor such as a fiber-Bragg grating sensor or another sensor as known to those of skill in the art. In one aspect of the disclosure, rather than employ an LG 110, as described above, the sensor 510 and the access tool 300 incorporating such as sensor 510 may be employed to determine the position of the catheter 102 of the catheter guide assembly 106 as it is being navigated through the airways of a patient. Further, even after navigation of the catheter 102 to a desired location proximate a portion of the airway disposed between the catheter 102 and the target tissue 202, the sensor 510 can be employed to track the movement of the dilating member 508 as it is being moved through the opening created in the airway by the piercing member 302 and tunneling to the target tissue 202.

Figure 6A:
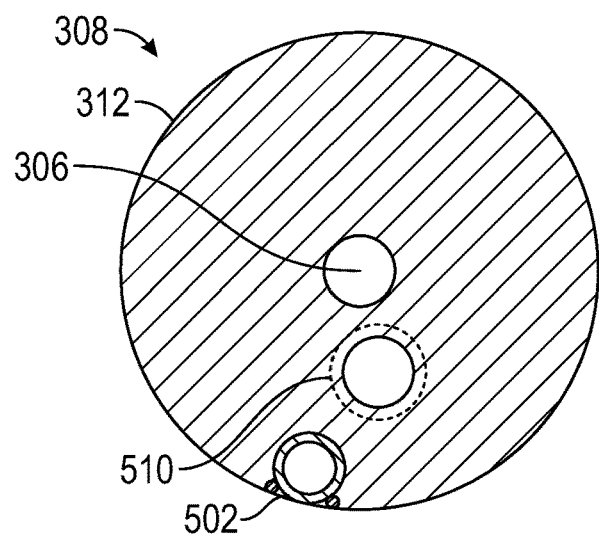
FIGS. 6A and 6B are cross-sectional views of a dilating member in accordance with the disclosure.
Figure 6B:
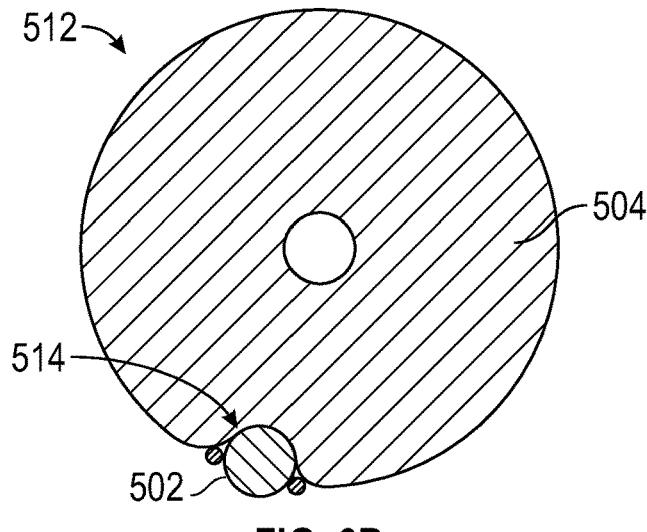

FIGS. 6A and 6B depict cross-sectional views of the dilating member 308 proximate its distal end. As seen in FIG. 6A, the piecing member 302 passes through the lumen 508 formed in the dilating member 308. The sensor 510 is secured in the dilating member 308 proximate a distal end of the pull-wire 502 which may be welded to the minimally traumatic tip 312 of the dilating member 308. FIG. 6B shows an alternative configuration of the pull-wire 502. In the embodiment of FIG. 6B, rather than forming a lumen within the catheter body 504, a channel may be formed on an exterior surface 512 of the catheter body 504 of the dilating member 308. The end of the pull-wire 502 may still be welded to the minimally traumatic tip 312, but the pull-wire runs in a C-shaped channel 514 which is open but still captures the pull-wire 502 while allowing the pull wire to be retracted to articulate the dilating member 308. As will be appreciated, the minimally traumatic tip 312 acts as a pull ring for the dilating member 308 to enable the articulation of the distal member 308.

The articulation of the dilating member 308 further assists in the user in manipulating the access tool 300 and particularly the minimally traumatic tip 312 of the dilating member 308 such that it can be maneuvered to point in a desired direction. As noted above, one aspect of the disclosure is directed to enabling access to target tissue 202, such as a lesion or tumor for both biopsy and therapy. In accordance with the disclosure, the access tool 300 can be inserted into the tumor or lesion utilizing the spring-loaded actuator 406 to cause the piecing member 302 and particularly the piercing tip 306 to pierce the outer shell of the tumor or lesion, and the dilating member 308 can be advanced over the piercing member 302. It is desirable to place for example a microwave ablation catheter, radio-frequency ablation catheter, a cryo-ablation catheter, or other treatment device in the center of a tumor or lesion. Utilizing the process described above, placement of the access tool 300 can be confirmed both via detection of the position of the sensor 510 and also via intraprocedural imaging such as via the fluoroscope 124 or a cone-beam CT imaging device. Once so placed, the catheter 102 may be advanced over the access tool 300 to secure the catheter 102 in the tumor. At this point the access tool 300 may be removed from the catheter guide assembly 106 and endoscope 108 and the treatment device (not shown) may be advanced through the catheter guide assembly 106 and catheter 102 for placement within the tumor or lesion so that effective and complete therapy may be undertaken.

While detailed embodiments are disclosed herein, the disclosed embodiments are merely examples of the disclosure, which may be embodied in various forms and aspects. For example, embodiments of an electromagnetic navigation system, which incorporates the target overlay systems and methods, are disclosed herein; however, the target overlay systems and methods may be applied to other navigation or tracking systems or methods known to those skilled in the art. Therefore, specific structural and functional details disclosed herein are not to be interpreted as limiting, but merely as a basis for the claims and as a representative basis for teaching one skilled in the art to variously employ the disclosure in virtually any appropriately detailed structure.

We claim:

1. A catheter navigation system comprising:
a catheter guide assembly including a catheter and configured to be received within a working channel of a bronchoscope;
an access tool configured to be received within the catheter of the catheter guide assembly, the access tool including a distal end and a proximal end, a dilating member having a minimally traumatic tip formed on the distal end, a lumen extending through the catheter, and a handle formed on a proximal end, and a piercing member sized for reception and translation within a lumen of the dilating member, the piercing member having a distal end, a proximal end, a piercing tip on the distal end of the piercing member, and a handle formed on the proximal end of the piercing member;
a rail including a plurality of slidable and lockable anchors, a first slidable and lockable anchor of the plurality of slidable and lockable anchors configured to connect to the catheter guide assembly, a second slidable and lockable anchor of the plurality of slidable and lockable anchors configured to connect to the handle of the dilating member and a third slidable and lockable anchor of the plurality of slidable and lockable anchors configured to connect to the handle of the piercing member;
a spring-loaded actuator, the spring-loaded actuator operably connecting the piercing member and the dilating member such that upon unlocking of the third slidable and lockable anchor, the handle of the piercing member is urged in the direction of the handle of the dilating member, and the piercing tip extends beyond the minimally traumatic tip of the dilating member; and
a stop configured for engagement with the rail and the piercing member to limit a distance the spring-loaded actuator drives the piercing member through the dilating member and a distance the piercing tip extends beyond the minimally traumatic tip of the dilating member.

2. The catheter navigation system of claim 1, further comprising a sensor secured in the minimally traumatic tip of the dilating member.

3. The catheter navigation system of claim 2, wherein the sensor is an electromagnetic sensor.

4. The catheter navigation system of claim 2, wherein the sensor is a shape sensor.

5. The catheter navigation system of claim 1, further comprising a pull-wire operably connected to the minimally traumatic tip of the dilating member.

6. The catheter navigation system of claim 5, further comprising a lumen formed in the dilating member for receiving the pull-wire.

7. The catheter navigation system of claim 5, further comprising an open groove formed on an exterior surface of the dilating member for receiving and retaining the pull-wire.

8. An access tool comprising:

a dilating member having proximal and distal ends, a minimally traumatic tip formed on the distal end, a lumen, a handle formed on the proximal end, and a piercing member having a proximal end and a distal end and sized for reception and translation within the lumen of the dilating member, the piercing member having a piercing tip on the distal end and a handle formed on the proximal end;

a rail including a plurality of slidable and lockable anchors, a first slidable and lockable anchor of the plurality of slidable and lockable anchors configured to connect to the handle of the dilating member and a second slidable and lockable anchor of the plurality of slidable and lockable anchors configured to connect to the handle of the piercing member; and a spring-loaded actuator, the spring-loaded actuator operably connecting the piercing member and the dilating member such that upon unlocking of the second slidable and lockable anchor, the handle of the piercing member is urged by a spring of the spring-loaded actuator in the direction of the handle of the dilating member, and the piercing tip extends beyond the minimally traumatic tip of the dilating member.

9. The access tool of claim 8 further comprising a stop configured for engagement with the rail and the piercing member to limit a distance the spring-loaded actuator drives the piercing member through the dilating member and a distance the piercing tip extends beyond the minimally traumatic tip of the dilating member.

10. The access tool of claim 8, further comprising a sensor secured in the minimally traumatic tip of the dilating member.

11. The access tool of claim 10, wherein the sensor is an electromagnetic sensor.

12. The access tool of claim 10, wherein the sensor is a shape sensor.

13. The access tool of claim 8, further comprising a pull-wire operably connected to the minimally traumatic tip of the dilating member.

14. The access tool of claim 13, further comprising a second lumen formed in the dilating member for receiving the pull-wire.

15. The access tool of claim 13, further comprising an open groove formed on an exterior surface of the dilating member for receiving and retaining the pull-wire.

16. An access tool comprising:

a dilating member having a proximal end and a distal end, a lumen, a minimally traumatic tip formed on the distal end, and a handle formed on the proximal end and a piercing member having a proximal end and a distal end and sized for reception and translation within the lumen of the dilating member, the piercing member having a piercing tip on the distal end and a handle formed on the proximal end; and a spring-loaded actuator, the spring-loaded actuator operably connecting the piercing member and the dilating member such that upon actuation the piercing member is urged by a spring of the spring-loaded actuator in a direction of the dilating member, and the piercing tip extends beyond the minimally traumatic tip of the dilating member.

17. The access tool of claim 16 further comprising a stop configured for engagement with the piercing member to limit a distance the spring-loaded actuator drives the piercing member through the dilating member and a distance the piercing tip extends beyond the minimally traumatic tip of the dilating member.

18. The access tool of claim 16, further comprising a sensor secured in the minimally traumatic tip of the dilating member.

19. The access tool of claim 18, wherein the sensor is an electromagnetic sensor.

20. The access tool of claim 16, further comprising a pull-wire operably connected to the minimally traumatic tip of the dilating member.

* * * * *